United States Patent [19]

Graber et al.

[11] 4,309,213

[45] Jan. 5, 1982

[54] PROCESS OF ENCAPSULATION BY INTERFACIAL POLYCONDENSATION

[75] Inventors: Gerard Graber, Lyons; Bernard Chatenet, Ecully; Philippe Pellenard, Decines, all of France

[73] Assignee: Rhone Poulenc Agrochimie, Lyons, France

[21] Appl. No.: 973,164

[22] Filed: Dec. 26, 1978

[30] Foreign Application Priority Data

Dec. 30, 1977 [FR] France .................................. 77 39950

[51] Int. Cl.$^3$ ..................... A01N 47/30; A01N 25/10; B01J 13/00
[52] U.S. Cl. ......................................... 71/120; 71/65; 71/79; 71/DIG. 1; 424/32; 424/225; 106/14.5; 106/15.05; 106/18.11; 106/19; 106/20; 252/316; 252/522 R; 426/540
[58] Field of Search ............. 71/120, DIG. 1; 424/32, 424/225; 252/316

[56] References Cited

U.S. PATENT DOCUMENTS

| | | | |
|---|---|---|---|
| 3,575,882 | 4/1971 | Vandegaer et al. | 424/32 |
| 3,577,515 | 5/1971 | Vandegaer | 424/32 |
| 3,607,776 | 9/1971 | Santo | 424/32 |
| 3,901,687 | 8/1975 | Bailey | 71/120 |
| 4,107,292 | 8/1978 | Nemeth | 424/32 |

FOREIGN PATENT DOCUMENTS 2312059  3/1972  Fed. Rep. of Germany .

OTHER PUBLICATIONS

Morrison et al., "Organic Chemistry", pp. 590–591, 910–911, (1966).
Pianka, "Insecticidal S-Chloromethyl etc."; (1970), CA72, No. 100883v. (1970).
Duerr, "Herbicidal N—(p-isopropyl) etc.", (1971), CA75, No. 151571m. (1971).
Scher, C.A., vol. 87:40412p, (Oct. 1975), p. 40421, Abst. of German OLS 2,648,562.
Lemin et al., C.A., vol. 80:79155m, (Dec. 1973), p. 84, Abstract of U.S.P. 3,776,716.
Scher, C.A., vol. 80:79164q, (Sep. 1973), pp. 84–85, Abstract OLS 2,312,059.
Murthy et al., "Organic Chem. Made Simple", (1962), p. 258.

*Primary Examiner*—Glennon H. Hollrah
*Attorney, Agent, or Firm*—Browdy and Neimark

[57] ABSTRACT

The process for the encapsulation of a liquid hydrophobic substance involves, in a first stage, dispersing an organic phase containing the liquid hydrophobic substance to be encapsulated and at least one polyfunctional hydrophobic monomer having functional groups containing the carbonyl or sulphonyl group, in an aqueous phase containing a polyfunctional amine in which the amine functions have been rendered inactive by salification, and subsequently starting polycondensation by liberating the amine functions through the addition, to the aqueous phase, of an equivalent amount of a base which is stronger than the amine. The process has application to the preparation of compounds which can be used especially in the field of plant health.

30 Claims, No Drawings

PROCESS OF ENCAPSULATION BY INTERFACIAL POLYCONDENSATION

The present invention relates to a process for the encapsulation of liquid substances by interfacial polycondensation. It also relates to the capsules obtained by this process.

The encapsulation of liquid substances by interfacial polycondensation was discovered long ago. The principle of the method consists in bringing into contact a phase containing the liquid substance to be encapsulated and a polycondensation reagent, with another phase which is immiscible with the first and contains a second reagent capable of reacting with the first to give a polycondensation product. When the two phases are brought into contact, the two compounds react at the interface of the phases and, by polycondensation, create a wall of polymer around the drops of liquid substances. The capsules obtained can then be washed and dried before use. In the most frequent case, the disperse phase is organic, whilst the second phase, used as the dispersion medium, is aqueous. In other words, the reaction takes place in a dispersion of the "oil-in-water" type.

The polymer constituting the wall of the capsules obtained can be a poly(sulphon)amide, a polyester, a polyether, a polyurethane or a polyurea or copolymers containing at least two types of unit chosen from ester, ether, (sulphon)amide, urethane and urea. The reagents which can be used in the formation of the above polymers or copolymers must be at least difunctional. The presence of more than two functional groups causes the polymer chains to crosslink with one another.

Various particular methods for carrying out this general technique have been proposed: one consists in carrying out the dispersion and the reaction simultaneously. In a first stage, an organic phase is prepared which contains the substance to be encapsulated, optionally with a solvent, and the hydrophobic reagent, and this phase is then dispersed in the aqueous phase containing the hydrophilic reagent. In this case, the reaction therefore takes place at the actual moment of dispersion. The fact that the two phenomena occur simultaneously exhibits the disadvantage that it leads to capsules having an excessively wide distribution of diameters.

In order to overcome this disadvantage, another technique consists in carrying out the process in two stages so as to separate the dispersion operation from the actual reaction. In other words, the organic phase, as described above, is initially dispersed in water, and the hydrophilic reagent is then added to the dispersion.

A process for encapsulation by interfacial polycondensation with a polyurea is also known, which consists, in a first stage, in dispersing in water an organic phase containing the substance to be encapsulated, and at least one polyisocyanate, and then, in a second stage, in starting the reaction by hydrolysing some of the functional groups of the polyisocyanate or polyisocyanates into amine functions, the latter then reacting immediately with the remaining polyisocyanates to give the polyurea.

This process exhibits the disadvantage that it employs a slower reaction (polyisocyanates with water) and that it consequently requires several additional conditions (temperature and catalyst) which complicate the manner in which it is carried out.

However, the techniques for the encapsulation of substances by interfacial polycondensation have found applications in the most diverse fields such as, for example, inks, dyestuffs, paints, perfumes, foodstuffs, pharmaceutical products and products for plant health.

This technique is particularly suitable for this last field, because it provides compositions which liberate the active ingredients (insecticides, herbicides, fungicides and the like) in a controlled manner (passage across the polymer wall), thus permitting, in particular, a reduction in the amounts and a lowering of the toxicity on handling and on the crops. Furthermore, compared with other compositions which combine active ingredients and polymers, the compositions obtained by this technique exhibit the advantage that they use a much smaller amount of polymer, and this leads to a smaller amount of waste products in the environment of the treated crops.

The value of these applications therefore requires an improvement in the former techniques.

The subject of the present invention is therefore to provide a process which does not exhibit the disadvantages of these techniques.

It relates to the process for the encapsulation of a liquid hydrophobic substance by interfacial polycondensation, which consists, in a first stage, in dispersing, in an aqueous phase, an organic phase containing the liquid hydrophobic substance to be encapsulated and at least one polyfunctional hydrophobic reagent having functional groups containing the carbonyl or sulphonyl group, and then, in a second stage, in causing the polycondensation of the hydrophobic reagent with at least one polyfunctional amine as a hydrophilic reagent, characterised in that, in the first stage, the aqueous phase contains the polyfunctional amine, the amine functions of which have been rendered unreactive by salification, and in that, in the second stage, the polycondensation is started by liberating the amine functions through the addition, to the aqueous phase, of an equivalent amount of a base which is stronger than the amine.

For the purpose of the present invention, the term "substance" is to be understood as meaning a liquid or solid compound which is essentially hydrophobic, that is to say virtually insoluble in water, and which is inert towards the hydrophobic reagents. If this substance is itself a liquid, it can be used in the process either directly or in the form of a solution or dispersion. If it is a solid, it must be either dissolved or suspended in an organic solvent beforehand. Therefore, in order to carry out the invention, the substance will always be in the form of a liquid and it is in this sense that the term "liquid substance" is applied in the description to this presentation of the substance. Any substance satisfying the above conditions is suitable for carrying out the invention, regardless of its final application, for example as a dyestuff, ink, pharmaceutical product, foodstuff, paint, cosmetic product, adhesive, catalyst, cleaning product, fireproofing agent, antioxidant and, in particular, as an active ingredient for plant health, such as a herbicide, insecticide, fungicide or growth regulator. Particularly valuable results have been obtained with insecticides such as parathion-methyl and Chlormephos and with the herbicide Isoproturon. As the solvent which can be used for bringing the substance into a liquid form (solution or dispersion), there may be mentioned aliphatic or aromatic, hydrophobic organic solvents, for example cyclohexane, tetrachloroethylene, xylene, carbon tetrachloride, chloroform and 1,2-dichloroethane.

The hydrophobic reagents which can be used according to the invention are at least difunctional in order to enable the polycondensation reaction to take place. Furthermore, the functional groups must contain the carbonyl group

or sulphonyl group

In practice, since they must react with amine functions, the functional groups are respectively

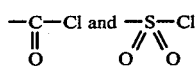

groups which are respectively characteristic of the carboxylic and sulphonic acid chlorides, and/or —N=C=O groups which are characteristic of the isocyanates.

In the first case, a poly(sulphon)amide will therefore be obtained; in the second case, a polyurea will be obtained. The process according to the invention can simultaneously employ two different types of hydrophobic reactant, for example a polyfunctional acid chloride with a polyfunctional isocyanate. A mixed polycondensation product, referred to as a poly(sulphon)amide-urea, is then obtained. Furthermore, the hydrophilic reagents are primary or secondary amines which are at least difunctional and preferably di- or tri-functional.

In general terms, the crosslinking index of the polycondensation products is higher, the larger the number of functional groups carried by the hydrophobic and hydrophilic reagents. The term crosslinking index is to be understood as meaning half the sum of the mean number of functional groups per molecule of the hydrophilic reagents and of the hydrophobic reagents. In practice, the crosslinking of the polymeric material of the wall of the capsule is influenced particularly by varying the number of functional groups in the acid chlorides and, preferably, in the isocyanates and amines, this crosslinking largely determining the rate of liberation of the encapsulated substance.

The polyfunctional acid chlorides which can be used according to the invention mainly include chlorides of saturated or unsaturated, aliphatic carboxylic acids, or of aromatic carboxylic acids, which can contain from 2 to 36 carbon atoms. The preferred aliphatic acids are linear acids. Examples of diacids which may be mentioned are, for the aliphatic diacids, oxalic acid, succinic acid, adipic acid, azelaic acid, sebacic acid, undecanedioic acid and dimeric acid (namely the dimer of linoleic acid), and, for the aromatic diacids, terephthalic acid. Examples of triacids which may be mentioned are trimesic acid and citric acid. Within the scope of the invention, it is also possible to employ chlorides of sulphonic acids such as benzene-1,3-disulphonic acid and benzene-1,3,5-trisulphonic acid.

The organic polyfunctional isocyanates which can be used as hydrophobic reagents in the present process include aromatic isocyanates, in particular aromatic diisocyanates and triisocyanates, aliphatic diisocyanates, in particular high molecular weight, linear aliphatic diisocyanates, and prepolymers having a terminal isocyanate group, which are obtained by reacting a polyester, a polyether, a polyesterether having terminal hydroxyl groups, with a molecular weight of between 500 and 4,000, or mixtures of these polymers, with polyfunctional isocyanates.

Examples which may be mentioned are 1-chloro-2,4-diisocyanatobenzene, 4,4′-diisocyanatodiphenylmethane, 1,6-diisocyanatohexane, diisocyanatonaphthalenes and, preferably, 2,4- or 2,6-diisocyanatotoluene or mixtures containing respectively 60/80% of the 2,4 isomer and 40/20% of the 2,6 isomer, and also polymethylene-polyphenylisocyanate.

These organic polyisocyanates can either be used by themselves or in mixtures. For example, mixtures based on polymethylene-polyphenylisocyanate and on diisocyanatotoluene (containing 80% of the 2,4 isomer and 20% of the 2,6 isomer) make it possible to obtain capsule walls possessing good properties of controlled liberation of the substance.

The amount of hydrophobic reagent(s) which is to be employed in the process according to the invention determines the proportion of wall in the capsule. In practice, proportions of 5 to 50% by weight of the organic phase will be preferred. In fact, below 5%, the wall of the capsules obtained no longer has adequate mechanical characteristics; above 50%, the proportion of polymer becomes economically less valuable and, in many cases, of no technical value.

As polyfunctional amines which can be used as hydrophilic reagents for the purpose of the present invention, there may be mentioned, in particular, difunctional aliphatic or aromatic amines such as, for example, preferably, ethylenediamine but also phenylenediamines, toluenediamines, hexamethylenediamine or piperazine, and also amines having more than two functional groups, such as, preferably, diethylenetriamine but also bis-(hexamethylene)-triamine, 1,3,5-triaminobenzene, 2,4,6-triaminotoluene and the like.

In order to carry out the process according to the present invention, each of the two immiscible phases is initially prepared. The organic phase is obtained by mixing the liquid substance to be encapsulated, with the hydrophobic reagent or reagents in the proportions indicated above. This mixing takes place with dissolution, if the liquid substance is homogeneous (with or without solvent), or with dispersion, if the liquid substance is itself a dispersion or suspension in an organic solvent.

The aqueous phase is prepared by dissolution of a water-soluble salt which is obtained beforehand by salifying the polyfunctional amine with a strong inorganic acid, such as a hydrogen halide acid, in particular hydrochloric acid, or a perhalic acid, or a strong organic acid, in particular acetic acid, methanesulphonic acid, benzenesulphonic acid or para-toluenesulphonic acid. The solution thus obtained is generally acid, the acidity of the amine salt being a function of that of the salifying acid and of the basicity of the amine. Anionic, cationic or non-ionic surface-active agents which are customary in interfacial polycondensation processes can also be added to this aqueous phase. However, in many cases, these adjuvants are not essential.

On the other hand, the addition of a protective colloid to the aqueous phase is frequently advisable and this can be carried out either before or after dispersion. Examples of suitable protective colloids which may be mentioned are polyacrylates, methylcellulose, polyvinyl alcohol which is optionally more or less esterified or etherified, and polyacrylamide. The adjuvants are usually added at the rate of 0.1 to 5% by weight of the aqueous phase. In some cases, the properties of these colloids can make it necessary to additionally employ anti-foam agents, in particular those based on silicones.

After adding all these ingredients to the water, the aqueous phase can advantageously be homogenised by stirring.

This is then followed by the first stage which is characteristic of the process according to the invention, that is to say dispersion, for example by running the organic phase into the aqueous phase, preferably whilst stirring vigorously, for example using a turbine stirrer, in order to thoroughly distribute, in the medium, the droplets which form, and in order to determine and regularise their size. The stirring force is advantageously regulated so that the droplets have a dimension ranging from about 1 micron to 100 microns. Larger dimensions are possible, but most frequently provide no additional advantage.

Once dispersion is complete, the polycondensation reaction is started by liberating the polyfunctional amine or amines through the addition, to the dispersion medium, of a base which is at least as strong as the amine functions of the hydrophilic reagent. This base can either be a hydroxide, preferably an alkali metal hydroxide, or a salt of a weak acid and a strong base. In practice, sodium hydroxide, potassium hydroxide or ammonia is used. Of course, this base must be added to the dispersion in an approximately stoichiometric amount.

After the start of the reaction, the stirring of the dispersion is continued, but in a more moderate manner, for a period of about 1 to 5 hours at a temperature which is normally between about 0° C. and ambient temperature. Although theoretically possible, high temperatures are not desirable within the scope of the present invention, because they assist side reactions and, in certain cases, are likely to degrade the substance to be encapsulated.

The process described above has been presented as a discontinuous operation, but it can be adapted for continuous operation, in particular by regulating the rate of introduction of the reagents, the rate at which the capsules are drawn off and the speed at which the dispersion is stirred.

Finally, the capsules obtained in accordance with the process are optionally separated from the aqueous phase, in a manner which is in itself known, and then washed until the pH of the washings is approximately neutral and dried. They are then ready for use, either as obtained or in an aqueous dispersion or emulsion, depending on the nature and the properties of the encapsulated substance, and also on the desired application.

The following examples are given by way of indication in order to illustrate the invention.

EXAMPLE 1

The following mixtures A, B and C are prepared just before use:

| Mixture A | |
|---|---|
| distilled water | 300 g |
| polyvinyl acetate hydrolysed to the extent of 88 mol % | 1.5 g |
| anti-foam silicone oil | 8 drops |
| ethylenediamine hydrochloride | 33.2 g |
| diethylenetriamine hydrochloride | 30.9 g |
| Mixture B | |
| O,O-dimethyl O-(p-nitrophenyl) thiophosphate (parathion-methyl) in xylene solution (80% of active ingredient) | 228 g |
| polymethylene-polyphenylisocyanate | 33 g |
| Mixture C | |
| distilled water | 100 g |
| sodium hydroxide pellets | 37.4 g |

Solution A is introduced into a one liter cylindrical reactor equipped with a turbine stirrer having a high rate of shear, and with a frame stirrer for carrying out more moderate stirring.

The organic solution B is rapidly run into this solution, stirred by the turbine stirrer. After about 45 seconds, the dispersion is satisfactory, the turbine is stopped and the experiment is continued using the frame stirrer. As soon as the turbines are stopped, the aqueous sodium hydroxide solution C is rapidly run in.

After a reaction time of 3 hours, the microcapsules are filtered off and washed until the pH of the washings is neutral.

Capsules $C_1$, containing parathion-methyl, are obtained, the sizes of which range from 20 to 40 microns and in which the crosslinking index of the polyurea constituting the wall is 2.53.

EXAMPLE 2

The procedure of Example 1 is followed, using the following mixtures A, B and C:

| Mixture A | |
|---|---|
| distilled water | 400 ml |
| polyvinyl acetate hydrolysed to the extent of 88 mol % | 1.5 g |
| anti-foam silicone oil | 8 drops |
| ethylenediamine hydrochloride | 43 g |
| Mixture B | |
| O,O-dimethyl O-(p-nitrophenyl) thiophosphate in xylene solution (80% of active ingredient) | 164.5 g |
| sebacoyl chloride | 19.3 g |
| Mixture C | |
| distilled water | 133 g |
| sodium hydroxide pellets | 32.3 g | are similar to those above and the wall of which is a linear polyamide (crosslinking index 2.00).

EXAMPLE 3

The procedure of Example 1 is followed, using the following mixtures A, B and C:

| Mixture A | |
|---|---|
| distilled water | 400 g |
| polyvinyl acetate hydrolysed to the extent of 88 mol % | 1.5 g |
| anti-foam silicone oil | 8 drops |
| ethylenediamine hydrochloride | 43 g |
| Mixture B | |

-continued

| | |
|---|---|
| O,O-dimethyl O-(p-nitrophenyl) thiophosphate in xylene solution (80% of active ingredient) | 164.5 g |
| polymethylene-polyphenylisocyanate | 7.2 g |
| sebacoyl chloride | 19.3 g |
| Mixture C | |
| sodium hydroxide pellets | 32.2 g |
| distilled water | 133 g |

Capsules $C_3$ are obtained, the dimensions of which are similar to those above and the wall of which is a polyamide-urea having a crosslinking index of 2.07.

EXAMPLE 4

The procedure of Example 1 is followed, using the following mixtures A, B and C:

| | |
|---|---|
| Mixture A | |
| distilled water | 400 ml |
| polyvinyl acetate hydrolysed to the extent of 80 mol % | 1.75 g |
| anti-foam silicone oil | 8 drops |
| ethylenediamine hydrochloride | 21.5 g |
| diethylenetriamine hydrochloride | 22.9 g |
| Mixture B | |
| O,O-dimethyl O-(p-nitrophenyl) thiophosphate in xylene solution, containing 80% of active ingredient | 164.5 g |
| polymethylene-polyphenylisocyanate | 7.2 g |
| sebacoyl chloride | 19.3 g |
| Mixture C | |
| distilled water | 130 ml |
| sodium hydroxide pellets | 39 g |

Capsules $C_4$ are obtained, the dimensions of which are similar to those above and the wall of which is a polyamide-urea having a crosslinking index of 2.27.

EXAMPLE 5

Biological Test

The residual biological activity of parathion-methyl encapsulated in accordance with the process of the invention illustrated in Examples 1, 3 and 4 ($C_1$, $C_3$, $C_4$) is studied in comparison with the commercial formulation as an emulsifiable concentrate containing 400 g/liter of active ingredient.

The capsules are used in the form of an aqueous suspension containing 200 g/liter of active ingredient.

In a spray pass, bean plants at the stage of two fully open cotyledon leaves are treated, after having destroyed the apical bud, with an aqueous suspension or emulsion of the active ingredient to be tested, until dripping wet, in accordance with a scale of doses expressed in g/hl. Discs of leaf are taken from the treated plants after a variable time, either immediately (D0) or after an increasing number of days (D+1, D+4, D+8, D+15, D+21 or D+30), and each disc is placed in a Petri dish, into which are introduced 5 cotton-moth (Spodoptera littoralis) caterpillars, at the 3rd larval stage, in order to check the effectiveness of the residual material as an insecticide. Each Petri dish is then kept in the dark in an enclosure at a temperature of 25° C. and a relative humidity of 70%. 48 hours after contact, the dead and live caterpillars are counted. The following table gives the mortality rates for each formulation tested, at a dose of 50 g/hl of active ingredient, as a function of time.

| Reference of the composition used | Crosslinking index of the capsules | % mortality at | | | | | | | |
|---|---|---|---|---|---|---|---|---|---|
| | | D0 | D + 1 | D + 2 | D + 4 | D + 8 | D + 15 | D + 21 | D + 30 |
| $C_1$ | 2.53 | 100 | 100 | 100 | 100 | 100 | 100 | 100 | 100 |
| $C_3$ | 2.07 | 100 | 100 | 70 | 50 | 40 | 40 | 40 | 40 |
| $C_4$ | 2.27 | 100 | 100 | 100 | 100 | 100 | 100 | 100 | 100 |
| Commercial control | — | 100 | 0 | 0 | 0 | | | | |

This table clearly shows that, under the conditions of the example, there is a remarkable increase in the residual activity (total activity after one month), whereas the reference commercial formulation is inactive as from the day after the treatment.

Furthermore, the tests of acute oral toxicity in rats have shown that the encapsulated formulation has an $LD_{50}$ of about 38 mg of active ingredient/kg, that is to say about seven times that of the commercial formulation, also expressed in equivalents of pure parathion-methyl. In other words, the formulation according to the invention is seven times less toxic than the reference, and this is remarkable.

EXAMPLE 6

Encapsulation of a Volatile Insecticide

The procedure of Example 1 is followed, using the following mixtures A, B and C:

| | |
|---|---|
| Mixture A | |
| distilled water | 433 g |
| polyvinyl acetate hydrolysed to the extent of 85 mol % | 2 g |
| anti-foam silicone oil | 8 drops |
| ethylenediamine hydrochloride | 33.2 g |
| diethylenetriamine hydrochloride | 30.9 g |
| Mixture B | |
| S-chloromethyl O,O-diethyl phosphorothiolothionate (Chlormephos) | 170 g |
| polymethylene-polyphenylisocyanate | 33.8 g |
| Mixture C | |
| sodium hydroxide pellets | 37.4 g |
| distilled water | 100 g |

After filtration and washing, microcapsules are obtained, the wall of which is a polyurea having a crosslinking index of 2.53. The rate of liberation of the insecticide is substantially reduced.

EXAMPLE 7

Encapsulation of a Volatile Insecticide by a Polyurea

The procedure of Example 1 is followed, using the following mixtures A, B and C:

| Mixture A | |
|---|---|
| distilled water | 433 ml |
| polyvinyl acetate hydrolysed to the extent of 85 mol % | 2.00 g |
| anti-foam silicone oil | 6 drops |
| ethylenediamine hydrochloride | 33.2 g |
| diethylenetriamine hydrochloride | 30.3 g |
| Mixture B | |
| S-chloromethyl O,O-diethyl phosphorothiolothionate (Chlormephos) | 170 g |
| toluene diisocyanate | 8.8 g |
| polymethylene-polyphenylisocyanate | 25 g |
| Mixture C | |
| aqueous sodium hydroxide (9.875 N) | 99 ml |
| water | 38 ml |

After filtration and washing, the capsules ($C_7$) are formulated into an aqueous suspension containing 30% (weight/weight) of active ingredient.

EXAMPLE 8

Encapsulation of a Volatile Insecticide by a Polyamide-urea.

The procedure of Example 1 is followed, using the following mixtures A, B and C:

| Mixture A | |
|---|---|
| distilled water | 451 ml |
| polyvinyl acetate hydrolysed to the extent of 85 mol % | 1.75 g |
| anti-foam silicone oil | 6 drops |
| ethylenediamine hydrochloride | 21.5 g |
| diethylenetriamine hydrochloride | 22.9 g |
| Mixture B | |
| S-chloromethyl O,O-diethyl phosphoro-thiolothionate (Chlormephos) | 165 g |
| sebacoyl chloride | 8.9 g |
| polymethylene-polyphenylisocyanate | 17.6 g |
| Mixture C | |
| aqueous sodium hydroxide (9.875 N) | 73 ml |
| water | 18 ml |

After filtration and washing the capsules ($C_8$) are formulated into an aqueous suspension containing 30% (weight/weight) of active ingredient.

EXAMPLE 9

The residual biological activity of Chlormephos microencapsulated in accordance with the process illustrated in Example 8 is studied in comparison with a commercial formulation in the form of a granulate containing 5% by weight of active ingredient.

Loam is mixed, respectively, by grinding with an aqueous suspension of the capsules obtained in Example 8 and by stirring in the case of the granules. The mixing is carried out so that the dosage of active ingredient is the same in the two cases and equal to 2 kg/ha. The mixture is introduced into pots. On the surface of the treated earth there are placed, per pot, 50 four-day old larvae of flies (Musca domestica). Each test is carried out twice.

A check on the number of dead larvae in comparison with, as controls, those placed on the surface of earth placed in pots, but not previously treated with Chlormephos, is then carried out immediately (DO) and at the end of 30 (D+30) and 45 (D+45) days.

Under these conditions the following mortality rate is observed:

| | D0 | D + 30 | D + 45 |
|---|---|---|---|
| Encapsulated Chlormephos | 100 | 100 | 64 |
| Chlormephos granules | 100 | 76 | 16 |
| Control | 2 | 3 | 2 |

This Example shows clearly that Chlormephos encapsulated by the process of the invention possesses not only an immediate insecticidal activity, which is as good as Chlormephos granulate but which is also more persistent, even though the granules are known to ensure a progressive release of the active ingredient.

EXAMPLE 10

Test of Phytotoxicity in the Treatment of Seed Wheat

Pieces of filter paper placed at the bottom of Petri dishes are treated, by spraying, with 0.5 ml of a dispersion of an emulsifiable concentrate of Chlormephos capsules obtained in Example 8. In parallel, commercial Chlormephos granules (containing 5% by weight of active ingredient) are stuck by moistening onto filter papers placed at the bottom of Petri dishes. The surface of the filter papers and the quantity, in concentration of active ingredient applied, is calculated to correspond to a dosage of 10 kg/ha in treatment in the open field ("localized strip" treatment).

Seed wheat is placed on the filter paper.

The Petri dishes are re-covered with their lids and germination is allowed to take place, in darkness and at ambient temperature. At the end of 3 days, the general appearance of the young shoots is observed on a scale of notation from 0 to 6 (0=no phytotoxicity, 6=complete destruction of the young shoot).

Under these conditions it is observed that, at a dose of 10 kg/ha, the $C_8$ capsules containing Chlormephos show no phytotoxicity whereas the young shoots are completely destroyed, at the same dosage of active ingredient, with the commercial granule formulation.

EXAMPLE 11

Acute oral toxicity tests on white rats, strain IOPS OFA, with Chlormephos encapsulated according to the process described in Example 8 and with commercial Chlormephos (granules with 5% by weight active ingredient) show that the latter have an LD 50 (lethal dose to 50%) of 12 mg/kg whereas the encapsulated form only shows, under the same conditions, an LD 50 of about 1600 mg/kg. This example clearly illustrates the considerable reduction in toxicity brought about by the process of the invention which allows Chlormephos, intrinsically toxic, to be handled with a wide margin of safety.

EXAMPLE 12

Encapsulation of a Herbicide in Suspension in Xylene

The procedure of Example 1 is followed, using the following suspension B and solutions A and C:

| Solution A | |
|---|---|
| distilled water | 400 g |
| polyvinyl acetate hydrolysed to the extent of 88 mol % | 2 g |
| anti-foam silicone oil | 8 drops |
| ethylenediamine hydrochloride | 33.2 g |
| diethylenetriamine hydrochloride | 30.9 g |

| Suspension B | |
|---|---|
| xylene | 100 g |
| N-(p-isopropylphenyl)-N,N'-dimethylurea (Isoproturon) (2 to 10 μm) | 100 g |
| polymethylene-polyphenylisocyanate | 33.8 g |
| Solution C | |
| sodium hydroxide pellets | 37.4 g |
| water | 100 ml |

After filtration and washing, 379 g of an aqueous suspension of microcapsules are recovered, which contain 24.5% by weight of N-(p-isopropylphenyl)-N,N'-dimethylurea (Isoproturon). The wall of the microcapsules is a polyurea and the diameters are between 2 and 140 microns. The rate of liberation of the herbicide in water is substantially reduced.

EXAMPLE 13

Encapsulation of a Fireproofing Agent in Xylene Solution

The procedure of Example 1 is followed, using the following mixtures A, B and C:

| Mixture A | |
|---|---|
| distilled water | 400 g |
| polyvinyl acetate hydrolysed to the extent of 88 mol % | 2 g |
| anti-foam silicone oil | 8 drops |
| diethylenetriamine hydrochloride | 65.3 g |
| Mixture B | |
| xylene | 132.2 g |
| polymethylene-polyphenylisocyanate | 33.3 g |
| tris-(2,3-dibromopropyl) phosphate | 132.2 g |
| Mixture C | |
| water | 133 g |
| sodium hydroxide pellets | 36.9 g |

After filtration and washing until the pH of the washings is neutral, the product is dried at 60° C. in a stream of air.

This gives a powder which is dry to the touch and consists of 2 to 40μ capsules containing 76% by weight of fireproofing agent, the remainder being composed of traces of xylene and of polyurea constituting the walls of the capsules.

EXAMPLE 14

Encapsulation of an Anti-ozone Agent in Xylene Solution

The procedure of Example 1 is followed, using the following mixtures A, B and C:

| Mixture A | |
|---|---|
| distilled water | 400 ml |
| polyvinyl acetate hydrolysed to the extent of 88 mol % | 2 g |
| anti-foam silicone oil | 8 drops |
| diethylenetriamine hydrochloride | 52.2 g |
| Mixture B | |
| polymethylene-polyphenylisocyanate | 33.3 g |
| xylene | 150 g |
| triphenylphosphine | 90.1 g |
| Mixture C | |
| water | 133 g |
| sodium hydroxide pellets | 29.5 g |

After filtration and washing until the pH of the washings is neutral, the product is dried at 60° C. in a stream of air. This gives a powder which is dry to the touch and consists of 2 to 25μ microcapsules containing about 50% of triphenylphosphine, 27% of xylene and 23% of polyurea constituting the walls.

We claim:

1. In a process for the encapsulation of a liquid hydrophobic substance by interfacial polycondensation comprising in a first stage, dispersing, in an aqueous phase, an organic phase consisting essentially of the liquid hydrophobic substance to be encapsulated and at least one hydrophobic reagent having two or three functional groups selected from the groups consisting of carboxylic acid chloride, sulfonyl acid chloride, isocyanate and mixtures thereof; and then, in a second stage, causing the polycondensation of the hydrophobic reagent with at least one di- or tri-functional amine as a hydrophilic reagent, said liquid hydrophobic substance being inert to said hydrophobic reagent and the polycondensation product thereof:

the improvement wherein, prior to said hydrophobic reagent being brought into contact with said di- or tri-functional amine, said di- or tri-functional amine in the aqueous phase has its amine functions rendered unreactive by salification with hydrohalic acid and, in the second stage, the polycondensation is started by liberating the amine functions through the addition, to the aqueous phase, of an equivalent amount of an inorganic base which is stronger than the amine.

2. Process according to claim 1, wherein said liquid hydrophobic substance is a pure organic compound.

3. Process according to claim 1, wherein said liquid hydrophobic substance is a solution in an organic solvent.

4. Process according to claim 1, wherein said liquid hydrophobic substance is a dispersion or suspension in an organic solvent.

5. Process according to claim 1, wherein said hydrophobic reagent is a di- or tri- functional acid chloride.

6. Process according to claim 5, wherein said hydrophobic reagent is a chloride of a diacid.

7. Process according to claim 6, wherein said hydrophobic reagent is a chloride of an aliphatic diacid containing from 2 to 36 carbon atoms.

8. Process according to claim 7, wherein said hydrophobic reagent is a chloride of a linear diacid.

9. Process according to claim 8, wherein said hydrophobic reagent is sebacoyl chloride.

10. Process according to claim 6, wherein said hydrophobic reagent is a chloride of an aromatic diacid.

11. Process according to claim 1 wherein said hydrophobic reagent is a di- or tri- functional isocyanate.

12. Process according to claim 11, wherein said hydrophobic reagent is a diisocyanate.

13. Process according to claim 11, wherein said hydrophobic reagent is a triisocyanate.

14. Process according to claim 11, wherein two separate polyisocyanates are used as the hydrophobic reagents.

15. Process according to claim 1, wherein at least one di- or tri-functional acid chloride and at least one di- or tri- functional isocyanate are used simultaneously as the hydrophobic reagents.

16. Process according to claim 1, wherein said hydrophilic reagent is a diamine.

17. Process according to claim 1, wherein said hydrophilic reagent is a triamine.

18. Process according to claim 1, wherein two separate polyfunctional amines are used as the hydrophilic reagents.

19. Process according to claim 1, wherein said hydrophilic reagent is an aliphatic amine.

20. Process according to claim 19, wherein said amine functions have been rendered unreactive by salification with hydrochloric acid.

21. Process according to claim 1, wherein said liquid hydrophobic substance contains an active ingredient for plant health.

22. Process according to claim 21, wherein that active ingredient for plant health is an insecticide.

23. Process according to claim 22, wherein that the insecticide is parathion-methyl.

24. Process according to claim 22, wherein that insecticide is Chlormephos.

25. Process according to claim 21, wherein that active ingredient for plant health is a herbicide.

26. Process according to claim 25, wherein said herbicide is Isoproturon.

27. Process according to claim 1 wherein said hydrophobic reagent comprises 5-50% of said organic phase.

28. Process according to claim 27 wherein said dispersing of said organic phase in said aqueous phase is effected by stirring sufficiently vigorous to form droplets of 1 micron to 100 microns.

29. Process according to claim 28 wherein said polycondensation is effected over about 1-5 hours at 0° C. to ambient temperature.

30. Process according to claim 1 wherein said di- or tri-functional amine is already mixed into said aqueous phase and its amine functions rendered unreactive prior to said dispersing.

* * * * *

UNITED STATES PATENT AND TRADEMARK OFFICE
CERTIFICATE OF CORRECTION

PATENT NO. : 4,309,213

DATED : Jan. 5, 1982

INVENTOR(S) : GRABER et al

Page 1 of 2

It is certified that error appears in the above-identified patent and that said Letters Patent are hereby corrected as shown below:

Claim 22, line 1 (column 13), line 12, delete "that" and insert therefor --said--.

Claim 23, line 1 (column 13, line 14), delete "that the" and insert therefor --said--.

Claim 24, line 1 (column 13, line 16) delete "that" and insert therefor--said--.

UNITED STATES PATENT AND TRADEMARK OFFICE
CERTIFICATE OF CORRECTION

PATENT NO. : 4,309,213
DATED : Jan. 5, 1982
INVENTOR(S) : GRABER et al

It is certified that error appears in the above-identified patent and that said Letters Patent are hereby corrected as shown below:

Claim 25, line 1 (column 14, line 1) delete "that" and insert therefor --said--.

Signed and Sealed this

Fifteenth Day of March 1983

[SEAL]

Attest:

GERALD J. MOSSINGHOFF

Attesting Officer

Commissioner of Patents and Trademarks